US 8,422,755 B2

(12) United States Patent
Drozdzal et al.

(10) Patent No.: US 8,422,755 B2
(45) Date of Patent: Apr. 16, 2013

(54) SYSTEM AND METHOD FOR SYNCHRONIZING IMAGE SEQUENCES CAPTURED IN-VIVO FOR AUTOMATIC COMPARISON

(75) Inventors: Michal Drozdzal, Wroclaw (PL); Petia Radeva, Sant Cugat (ES); Jordi Vitria, Barcelona (ES); Fernando Azpiroz, Barcelona (ES); Carolina Malagelada, Barcelona (ES); Santiago Segui Mesquida, Ciutadella de Menorca (ES); Laura Igual-Munoz, Barcelona (ES)

(73) Assignee: Given Imaging Ltd., Yoqneam (IL)

( * ) Notice: Subject to any disclaimer, the term of this patent is extended or adjusted under 35 U.S.C. 154(b) by 127 days.

(21) Appl. No.: 13/154,544

(22) Filed: Jun. 7, 2011

(65) Prior Publication Data

US 2011/0305377 A1 Dec. 15, 2011

Related U.S. Application Data

(60) Provisional application No. 61/353,799, filed on Jun. 11, 2010.

(51) Int. Cl.
| G06K 9/00 | (2006.01) |
| A61B 1/04 | (2006.01) |
| H04N 9/64 | (2006.01) |
| A61K 49/00 | (2006.01) |

(52) U.S. Cl.
USPC ............... 382/128; 348/76; 348/715; 424/9.1

(58) Field of Classification Search ................... 382/128, 382/129, 130, 131, 132, 133, 134, 218; 600/109, 600/443, 449, 475, 477, 587; 348/76, 161, 348/715; 424/9.1, 9.341, 900
See application file for complete search history.

(56) References Cited

U.S. PATENT DOCUMENTS

| 5,604,531 A | 2/1997 | Iddan et al. |
| 7,009,634 B2 * | 3/2006 | Iddan et al. ................... 348/76 |

(Continued)

OTHER PUBLICATIONS

Michal Drozdzal, Laura Igual, Jordi Vitria, Carolina Malagelada, Fernando Azpiroz, Petia Radeva, *Aligning Endoluminal Scene Sequences in Wireless Capsule Endoscopy*, EEE Computer Society Workshop on Mathematical Methods in Biomedical Image Analysis (MMBIA10), CVPR, pp. 117-124, Jun. 13-18, San Francisco, USA, 2010.

(Continued)

*Primary Examiner* — Abolfazl Tabatabai
(74) *Attorney, Agent, or Firm* — Pearl Cohen Zedek Latzer, LLP

(57) ABSTRACT

A system and method for comparing captured sequences of in-vivo images with (e.g., template) sequences, for example, for computer-automated diagnosis. Captured in vivo images may be divided into a plurality of captured image sequences. For each of the plurality of captured sequences, the processor may assign a first and second set of scores to each frame in the captured sequence and align each frame in the captured sequence with one or more frames in the template sequence for which the comparisons therebetween generate the minimum scores in the first and second sets of scores. The processor may define a match between the template sequence and captured sequences having a combination of scores in the first and second sets of scores for the frames in the captured sets compared with the one or more aligned frames in the template sequence, which are below or above a threshold value.

21 Claims, 10 Drawing Sheets

U.S. PATENT DOCUMENTS

| | | | | |
|---|---|---|---|---|
| 8,290,228 | B2* | 10/2012 | Cohen et al. | 382/128 |
| 2009/0202117 | A1 | 8/2009 | Vilarino et al. | |
| 2009/0284589 | A1 | 11/2009 | Radeva et al. | |
| 2011/0044515 | A1 | 2/2011 | Spyridonos et al. | |

OTHER PUBLICATIONS

Yagi et al., "A diagnosis support system for capsule endoscopy", Inflammopharmacology 15: 78-83, 2007. DOI 10.1007/s10787-006-0010-5.

Kadous M., "A General Architecture for Supervised Classification of Multivariate Time Series", pp. 1-51, Sep. 1998.

Mackiewicz et al., "Colour and Texture Based Gastrointestinal Tissue Discrimination", ICASSP pp. 597-600, 2006.

Lowe, D., "Distinctive Image Features from Scale-Invariant Keypoints", pp. 1-28, Jan. 5, 2004.

Igual et al., "Eigenmotion-based Detection of Intestinal Contractions", pp. 1-8, 2007.

Keogh et al, "Indexing Large Human-Motion Databases", pp. 1-12. 2004.

Deselaers et al., "Learning Weighted Distances for Relevance Feedback in Image Retrieval", pp. 1-4, 2008.

Kellow et al., "Principles of applied neurogastroenterology: physiology/motility—sensation", Gut 45 (Suppl II):II17-II24, 1999.

Zhou et al, "Relevance Feedback in Image Retrieval: A Comprehensive Review", pp. 1-25, 2003.

Fu et al., "Scaling and Time Warping in Time Series Querying", pp. 1-25, Proceedings of the 31st VLDB Conference, Trondheim, Norway, 2005.

Liu et al., "SIFT Flow: Dense Correspondence across Different Scenes", ECCV 2008, Part III, LNCS 5304, pp. 28-42, 2008.

Hansen, M.B., "Small Intestinal Manometry", Physiol. Res. 51: 541-556, 2002.

Horster et al., "Unsupervised Image Ranking", pp. 1-8, 2009.

Drozdzal et al., "Towards Detection of Measurable Contractions using WCE", pp. 1-6, 2009.

Vilarino et al., "Cascade analysis for intestinal contraction detection", pp. 1-4, 2006.

V. Hai et al. "Adaptive control of video display for diagnostic assistance by analysis of capsule endoscopic images", In Proc. ICPR, pp. 980-983, 2006.

S. Hwang et al. "Blood detection in wireless capsule endoscopy using expectation maximization clustering", In Proc. of the SPIE, pp. 577-587, 2006.

G. Iddan et al. "Wireless capsule endoscopy", Nature, 405:417, 2000.

E. M. Quigley. "Gastric and small intestinal motility in health and disease", Gastroenterology Clinics of North America, 25:113-145, 1996.

F. Vilarino. "A machine learning approach for intestinal motility assessment", PhD thesis, UAB, Barcelona, 2006.

H. Vu, T. Echigo, and et al. "Contraction detection in small bowel from an image sequence of wireless capsule endoscopy", In Proc. of MICCAI, pp. 775-783, 2007.

U.S. Appl. No. 13/228,287, filed Sep. 8, 2011, Drozdzal et al.

Michal Drozdzal, Laura Igual, Jordi Vitria, Carolina Malagelada, Fernando Azpiroz, Petia Radeva, "*Aligning Endoluminal Scene Sequences in Wireless Capsule Endoscopy*", EEE Computer Society Wrokshop on Mathematical Methods in Biomedical Image Analysis (MMBIA10), CVPR, pp. 117-124, Jun. 13-18, San Francisco. USA, 2010.

Fernando Vilariño, Panagiota Spyridonos, Jordi Vitrià and Petia Radeva, "Self Organized Maps for Intestinal Contractions Categorization with Wireless Capsule Video Endoscopy", The 3rd European Medical and Biological Engineering Conference EMBEC'05, IFMBE Proc. Prague, Czech Republic, Nov. 20-25, 2005.

Michal Drozdzal, Petia Radeva, Santi Segui, Fernando Vilariño, Carolina Malagelada, Fernando Azpiroz, Jordi Vitria, "Towards Detection of Measurable Contractions using WCE". Fourth CVC Workshop on the Progress of Research & Development, pp. 1-6, CVCRD, Catalonia, Spain, Oct. 30, 2009.

Carolina Malagelada, Fosca De Iorio, Fernando Azpiroz, Anna Accarino, Santi Segui, Petia Radeva and Juan—R. Malagelada, "New Insight Into Intestinal Motor Function via Noninvasive Endoluminal Image Analysis," Gastroenterology, vol. 135, pp. 1155-1162, 2008.

\* cited by examiner

SYSTEM AND METHOD FOR SYNCHRONIZING IMAGE SEQUENCES CAPTURED IN-VIVO FOR AUTOMATIC COMPARISON

REFERENCE TO RELATED APPLICATION

This application claims the benefit of U.S. Provisional Patent Application No. 61/353,799, filed Jun. 11, 2010, which is incorporated herein by reference in its entirety.

FIELD OF THE INVENTION

The present invention relates to systems and methods for analyzing an image stream captured in-vivo. More specifically, the present invention relates to systems and methods for synchronizing a sequence of images captured in vivo with an image sequence.

BACKGROUND OF THE INVENTION

Peristalsis within a gastro-intestinal (GI) tract may transport swallowed food and may aid in digestion and eventual evacuation. Peristalsis may result in pressure waves or contractions moving along the GI tract, thereby resulting in motility of a bolus or other object within the GI tract. The bolus may include an in-vivo imaging device able to acquire and transmit images of, for example, the GI tract while the in-vivo imaging device passes through the GI lumen.

Certain pathological conditions may alter the normal motility within the GI tract. Lower than average motility may be caused by, for example, an obstruction, a blockage, or other pathological condition. Motility disorders may be caused by, for example, nervous disorders, and may not necessarily be easily visible. For example, intestinal disorders such as irritable bowel syndrome (IBS) have been linked to irregular contraction rates. For example, faster than average colon contractions rates are common in people with diarrhea-predominant IBS (IBS-D) and slower than average colon contractions rates are common in people with constipation-predominant IBS (IBS-C). Accordingly, a patient's contraction rate may be useful in diagnosing such intestinal disorders.

Some systems may compare a captured image sequence with a template sequence known to exhibit pathological behavior such as irregular contractions. A sequence match may indicate the likely presence of the pathological behavior in the captured sequence.

However, sequence comparison may be difficult for images captured by an autonomous wireless imaging devices, which typically passes through the body by natural peristalsis at unpredictable and often irregular speeds. With such irregular motion, the captured sequence and the template contraction sequence may be out-of-synch. For example, an opening of a contraction in one sequence may have the same play time or frame number as a closing of a contraction in another sequence. Accordingly, it may be difficult to automatically compare the misaligned frames in the sequences.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

Figure 1:
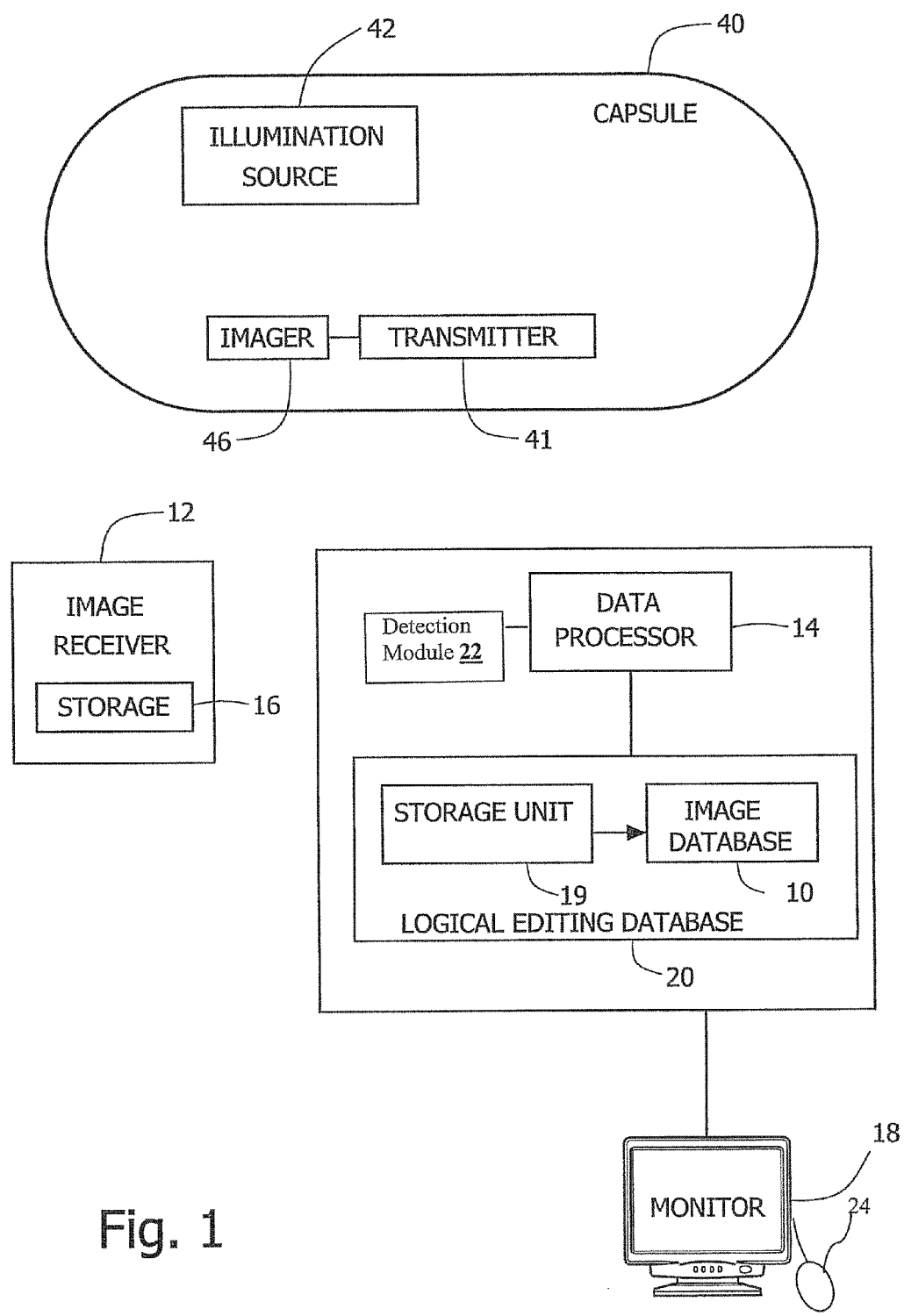
FIG. 1 is a schematic illustration of an in-vivo imaging system, according to an embodiment of the present invention.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

SUMMARY OF THE INVENTION

In an embodiment of the invention, a system and method is provided for comparing captured sequences of in-vivo images with (e.g., template) sequences, for example, for computer-automated diagnosis. The processor may divide captured in vivo images into a plurality of captured image sequences. For each of the plurality of captured sequences, the processor may assign a first and second set of scores to each frame in the captured sequence and align each frame in the captured sequence with one or more frames in the template sequence for which the comparisons therebetween generate the minimum scores in the first and second sets of scores. Each score in the first set of scores assigned to each frame in the captured sequence may be generated based on a comparison of anatomical structures of the frame in the captured sequence and anatomical structures of a (e.g., different) frame in the retrieved template sequence. Each score in the second set of scores assigned to each frame in the captured sequence may be generated based on a comparison of a change in anatomical structures between the frame in the captured sequence and a frame in the captured sequence consecutive thereto and a change in anatomical structures between a (e.g., different) pair of consecutive frames in the retrieved template sequence. The processor may define a match between the template sequence and captured sequences having a combination of scores in the first and second sets of scores for the frames in the captured sets compared with the one or more aligned frames in the template sequence, which are below a threshold value. A display may display the captured in vivo images, in sequence, as a moving image stream.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise computers or processors selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus. It will be appreciated that a variety of programming languages may be used to implement the teachings of the invention as described herein.

Embodiments of the invention may include an article such as a computer or processor readable non-transitory storage medium, or a computer or processor storage medium, such as for example a memory, a disk drive, or a USB flash memory, encoding, including or storing instructions, e.g., computer-executable instructions, which when executed by a processor or controller (for example, data processor 14 of FIG. 1), carry out methods disclosed herein.

Some embodiments of the present invention are directed to a typically swallowable in-vivo device, such as an autonomous swallowable imaging device. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in U.S. Pat. No. 7,009,634 and/or in U.S. Pat. No. 5,604,531, each of which are assigned to the common assignee of the present invention and each of which are hereby incorporated by reference in their entirety. Systems according to embodiments of the present invention may retrieve and process images captured by capsule endoscopes such as PillCam® SB or PillCam® SB2 commercially available from Given Imaging Ltd. Of course, devices and systems as described herein may have other configurations and other sets of components.

An autonomous in-vivo imaging device may move through the body lumen by natural peristalsis. Depending on the shape and movement of the endoluminal passageway, the imaging device may move at a variable speed, for example, relatively faster through larger unobstructed passages and relatively slower through narrow or blocked passageways. When the imaging device captures images at a fixed rate (for example, two or four frames per second (fps)), the physical distance between objects being imaged in consecutive frames is also variable, for example, relatively closer when the imaging device moves at a relatively slow speed and relatively farther when the imaging device moves at a relatively fast speed. When the images are combined, in sequence, to form a moving image, the disparity in the proximity of in-vivo objects may generate a skewed or distorted view of the body lumen.

Some mechanisms may compare anatomical objects or events (e.g., contractions of the lumen wall) between a captured segment and a template segment, for example, using a one-to-one frame comparison. Any disparity in the speed of the imager(s) that captured the image stream segments may cause a misalignment of anatomical objects and confusion in automatic comparison. For example, two contraction segments with nearly identical periodicity may be captured at two different imaging device speeds so that the contractions appear to have an out-of-phase periodicity (for example, one sequence shows the opening of a passageway, while the other sequence shows a closing of the passageway). In this example, due to the out-of-phase periodicity of the sequences, a match between these sequences may go undetected.

Other factors to consider for aligning image stream sequences may include detecting and matching the amount or type of deformation of the lumen passageway. During the passage of the imaging device, the passageway may be deformed by lateral contractions that include various degrees of opening, closing, rotating, twisting or bending (e.g., moving in the circumferential plane of the passage opening, which is typically in the imager's field of view) as well as by longitudinal contractions (e.g., moving along the length of the passage tube, which may or may not be in the imager's field of view).

Additional factors for alignment may include the direction of change of the image objects between consecutive frames. The change in direction may be caused by movement of the imager and/or the lumen wall itself.

Embodiments of the invention include systems and methods for synchronizing images sequences for comparison by aligning frames from different sequences. Frames may be aligned based on the similarity in anatomical structures between frames of different sequences, a direction of change of the image objects between consecutive frames in each sequence, and/or an amount of intestinal deformation between consecutive frames in each sequence. Out-of-phase or misaligned frames in one sequence may be re-aligned to be in-phase with similar content frames in a different sequence. For contraction sequences, the processor may synchronize frames from both sequences depicting the opening of a passageway and likewise, may synchronize frames from both sequences depicting the closing of a passageway.

Aligning sequences may include, for example, changing the indices of one or more frames or frame segments in the sequences so that frames with the same indices (which previously had different indices) are aligned. Aligning sequences may change the rate, time or length of an image sequence or a correspondence or mapping between frames in the sequences, for example, to elongate or shorten one or both sequences. In another embodiment, sequences may be aligned by defining a link between frames in one sequence using a pointer, index, flags, metadata, or other indicator of the corresponding one or more frames or the relative position of the one or more frames in the other sequence. Other methods of aligning sequences may be used.

In some embodiments, a sequence may be aligned by elongating, e.g., by inserting additional frames into the sequence, increasing the duration or time-slots associated with each frame, or defining an elongated mapping with another sequence. Extra frames inserted into the sequence may be a duplicate of a previous or subsequent frame or an average, merging or combination of adjacent previous and/or subsequent frames. An elongated mapping between sequences may define a correspondence between at least one frame in a first sequence to two or more frames in a second sequence. Instead of a one-to-one correspondence between frames of sequences, an elongated mapping may have a "one-to-many" correspondence. In some embodiments, additional frames may be moved to the memory storing the sequence or alternatively, an index may point to the additional frame in a separate memory.

Similarly, in some embodiments, a sequence may be aligned by shortening or compressing, e.g., by deleting or extracting frames from the sequence, averaging, merging or combining two or more frames into one, decreasing the play-time or time-slots associated with each frame, or defining a compressed mapping between the sequences. Frames deleted from the sequence may be for example frames that are most similar to a previous or subsequent frame or frames that are replaced by an average or combination thereof. A compressed mapping between sequences may define a correspondence between at least one group of two or more frames in a first sequence to a single frame in a second sequence. An elongated mapping may have a "many-to-one" correspondence.

Once the sequences are aligned, a processor may compare the content and features of the frames of each sequence in a captured image stream with each of one or more model or template sequences. A template sequence may be a sequence pre-stored in the system that is well defined and pre-analyzed and may be used as a reference for comparison with other sequences for the analysis, for example, of each individual patient's image stream. The processor may use pattern recognition and/or feature extraction logic to compare properties of the captured sequence with properties of the template sequences. The properties may include, for example, frame content, frame dynamics, color patterns, texture patterns, and/or geometric patterns or shapes within each frame or changes thereof between consecutive frames.

The plurality of template sequences may each be associated with, for example, one or more different pre-defined features, such as, frame content or dynamics features, motility features, structural features, or other features associated with images in the GI tract. When the difference between the compared sequences is below a predetermined threshold, the processor may indicate a match or suspected match between a captured sequence and a template sequence. The processor may diagnose or associate the captured sequence with the one or more features associated with the matching template sequence.

In one embodiment, the processor may use a scoring system to quantify and analyze the frame similarity features. For comparison, the template sequences may be matched with each captured sequence having the most similar score(s).

The processor may store, display or otherwise present the associated features or content scores to a user. The features may be presented as raw data or processed as a quantitative analysis or automatic computer-recognized diagnosis. In one embodiment, the processor may provide a map, table, or profile to display associated features with or adjacent to the corresponding sequences through the image stream. For example, similar to a time bar, a feature or motility bar may indicate a motility value corresponding to a frame or sequence being displayed. In one embodiment, the motility bar may be a one-dimensional (1D) graph. In one example, as the image stream is displayed, playing a sequence of frames over time, the motility values displayed also change to match the changing frames. In another embodiment, the time and motility values may be combined in a two-dimensional (2D) graph, for example, having an (x)-axis representing the playtime, such as a time bar, and a (y)-axis representing the motility value(s) for the displayed frame. The 2D motility graph may show the change in motility over the length of the entire moving image, the displayed portion, or the template sequence matching the current captured segment being displayed. In one example, the 2D motility graph, such as, a bar graph, may show values for a plurality of different motility features. Thus, as the movie plays, the motility bar may show an instantaneous measure of the imaging device motility or an overall GI tract motility curve.

Motility features may include, for example, the presence of contractions, the duration (e.g., length of the contraction sequence) and periodicity of opening and closing of the contractions, whether the contractions are symmetric (when opening and closing take the same or similar times) or asymmetric (when opening and closing take different times), the degree, radius, or direction of lumen deformation between the present frame and a consecutive frame, the presence of "wrinkles," static or tunnel scenes, "wall" sequences, bubbles or turbid sequences or other color or pattern features or changes, information about point motion estimated by optical flow (e.g., defining a point correspondence or point motion between consecutive frames determined by minimizing Sift descriptors of corresponding points in the consecutive frames), parameters of rigid and non-rigid transformations, decomposition of deformations using eigenmodes, etc. In some embodiments, one or more of these features or other image features may be used to align other sequences, e.g., not motility-related sequences such as pathology-related sequences (for example, sequences which may be indicative of a certain disease or condition of the GI tract).

As described, the processor may align frames for internal automatic sequence comparison. However, the aligned frames may or may not affect the display or viewing rate. In one embodiment, the processor may display the frames in their original captured rate, for example, displaying each frame in a sequence with equal play-time. In another embodiment, the processor may display the frames in their modified rate, e.g., a standardized rate or a predetermined rate of the template sequence. The modified rate may correspond to the elongated and/or compressed mapping, rate or length of the modified/aligned captured sequences. In another embodiment, the user may switch between displaying frames in the original captured rate (as possibly adjusted by standard display options such as pause or a user variable display rate) and the modified rate.

In some embodiments, metadata or other data associated or stored with frames in a sequence may indicate or store the re-alignment, e.g., changing frame indexing, timing, ordering, score or similarity measurements between the sequence and a template sequence, or other data associated with each frame (diagnoses, motility data, correspondences with pre-captured sequences) in the sequence. Changes to the metadata of a frame in one sequence may correspond to changes in the correspondence or alignment between the frames and other frames in another sequence. The metadata may be stored with the frames data, for example, in a storage unit.

Reference is made to FIG. 1, which schematically illustrates an in-vivo imaging system according to an embodiment of the invention.

According to some embodiments, a system may include a device, for example, an imaging device 40. Imaging device 40 may be a swallowable in-vivo imaging device, but other sorts of devices or suitable implementations may be used. Imaging device 40 may be autonomous, in that it may progress within the GI tract passively via peristalsis, and/or be not tethered or otherwise maneuvered by manipulation from outside the body. According to one embodiment, imaging device 40 may communicate with an external receiving and display system to provide display of data, control, or other functions. For example, power may be provided by an internal battery or a wireless receiving system. Other embodiments may have other configurations and capabilities.

Imaging device 40 may include an imager 46, for capturing images, an illumination source 42, for illuminating the body lumen, and a transmitter 41, for transmitting image and possibly other information to a receiving device. Transmitter 41 may include receiver capability, for example, to receive control information. An optical system, including, for example, lenses or mirrors, may aid in focusing reflected light onto the imager 46.

Preferably, located outside the patient's body in one or more locations, are an image receiver 12, preferably including an antenna or antenna array, an image receiver storage unit 16, a data processor 14, a data processor storage unit 19, and an image monitor 18, for displaying, for example, the images recorded by the imaging device 40. Preferably, the receiver 12 and image receiver storage unit 16 are small and portable, and are worn on the patient's body during recording of the images.

According to one embodiment of the invention, data processor 14, data processor storage unit 19 and monitor 18 are part of a personal computer or workstation which includes standard components such as a processor, a memory, a disk drive, and input-output devices, although alternate configurations are possible, and the system and method of the present invention may be implemented on various suitable computing systems. An input device 24 may receive input from a user (e.g., via a pointing device, click-wheel or mouse, keys, touch screen, recorder/microphone, other input components) and send corresponding commands to trigger control of the computer components, e.g., data processor 14.

Data processor 14 may include any standard data processor, such as a microprocessor, multiprocessor, accelerator board, or any other serial or parallel high performance data processor.

Image monitor 18 may be a computer screen, a conventional video display, or any other device capable of providing image or other data.

Preferably, the imager 46 is a suitable complementary metal-oxide-semiconductor (CMOS) camera, such as a "camera on a chip" type CMOS imager specified by Given Imaging Ltd. of Israel and designed by Aptina Corporation of California, USA. In alternate embodiments, the imager 46 may be another device, for example, a charge-coupled device (CCD).

The illumination source 42 may be, for example, one or more light emitting diodes, or another suitable light source.

In operation, imager 46 may capture images and send data representing the images to transmitter 41, which transmits images to receiver 12 using, for example, electromagnetic radio waves. Receiver 12 may transfer the image or other received data to storage unit 16. After a certain period of time of data collection, the image data stored in storage unit 16 may be sent to the data processor 14 or the data processor storage unit 19. For example, the image receiver storage unit 16 may be taken off the patient's body and connected to the personal computer or workstation which includes the data processor 14 and data processor storage unit 19 via a standard data link, e.g., a serial or parallel interface of known construction. The image data may then be transferred from the image receiver storage unit 16 to the image database 10 within data processor storage unit 19.

Data processor 14 may analyze the data, for example, according to the logical editing database 20, and provide the analyzed data to the image monitor 18, where for example, a health professional views the image data and/or corresponding analyzed data such as motility information or a computer-generated diagnosis. Data processor 14 may operate software which, in conjunction with basic operating software such as an operating system and device drivers, controls the operation of data processor 14. According to one embodiment, the software controlling data processor 14 may include code written, for example, in the C++ language and possibly alternative or additional languages, and may be implemented in a variety of known methods.

The image data collected and stored may be stored indefinitely, transferred to other locations, or manipulated or analyzed. Data processor 14 may use the images to diagnose pathological conditions of for example the GI tract, and, in addition, the system may provide information about the location of these pathologies. While using a system where the data processor storage unit 19 first collects data and then transfers data to the data processor 14, the image data is not viewed in real time, other configurations allow for real time viewing.

According to one embodiment, the imaging device 40 may collect a series of still images as it traverses the GI tract. The images may be later presented as, for example, a stream or sequences of images or a moving image of the traverse of the GI tract. The in-vivo imager system may collect a large volume of data, as the imaging device 40 may take several hours to traverse the GI tract. The imager 46 may record images at a rate of, for example, four to forty images per second (other rates, such as two frames per second, may be used). The imager 46 may have a fixed or variable frame capture and/or transmission rate. When the imager 46 has a variable or adaptive frame rate (AFR), the imager 46 may switch back and forth between frame rates, for example, based on parameters, such as the imaging device 40 speed, estimated location, similarity between consecutive images, or other criteria. A total of thousands of images, for example, 50,000 images, may be recorded. The image recordation rate, the frame capture rate, the total number of images captured, the total number of images selected if the moving image is edited, and the view time of the moving image, may each be fixed or varied.

Preferably, the image data recorded and transmitted by the imaging device 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by a one byte (i.e., 0-255) brightness value. According to one embodiment, images may be stored sequentially in data processor storage unit 19. The stored data may include one or more pixel properties, including color and brightness.

While, preferably, information gathering, storage and processing are performed by certain units, the system and method of the present invention may be practiced with alternate configurations. For example, the components gathering image information need not be contained in an imaging device, but may be contained in any other vehicle suitable for traversing a lumen in a human body, such as an endoscope, stent, catheter, needle, etc. Data processor storage unit 19 may store a series of images recorded by an imaging device 40. The images the imaging device 40 records as it moves through a patient's GI tract may be combined consecutively to form a moving image stream.

Figure 2A:
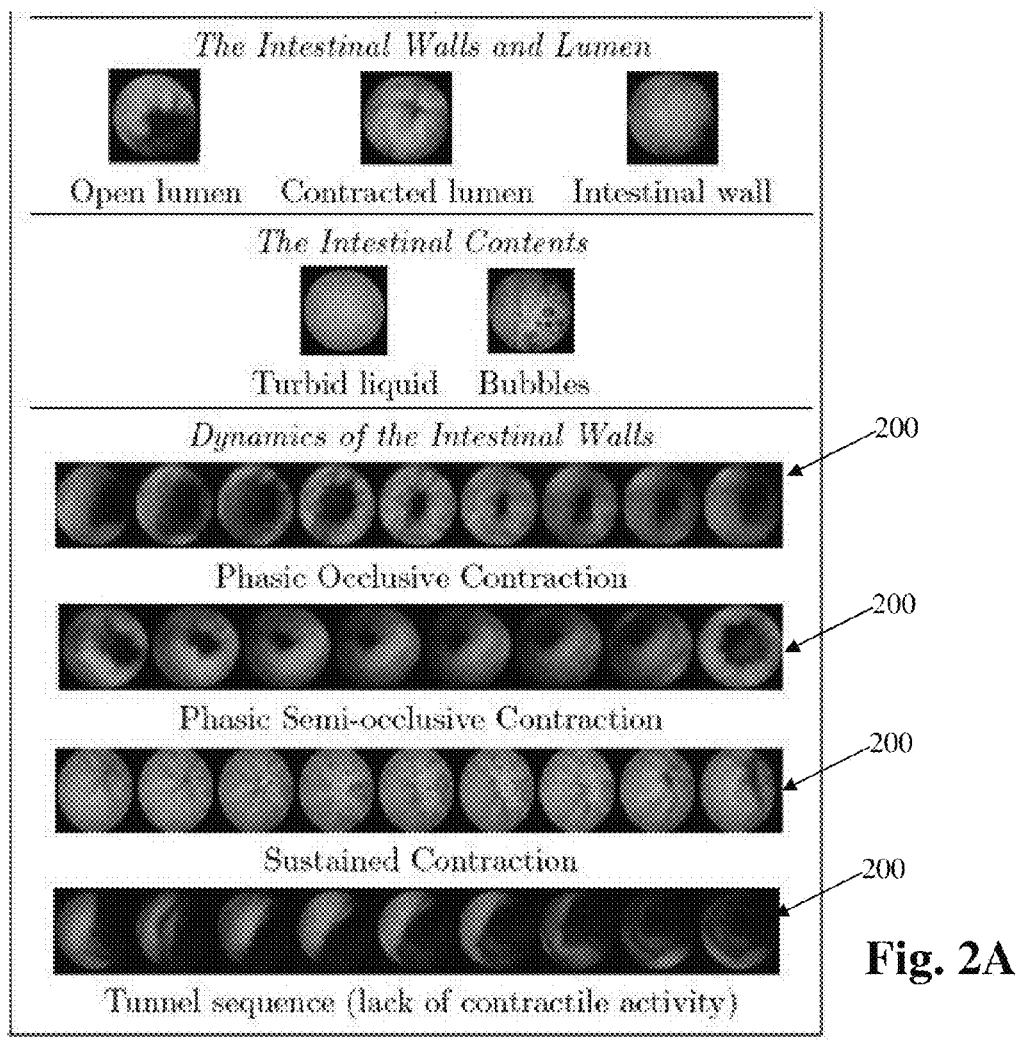
FIGS. 2A and 2B are pictures of template sequences and captured sequences, respectively, according to embodiments of the present invention.
Figure 2B:
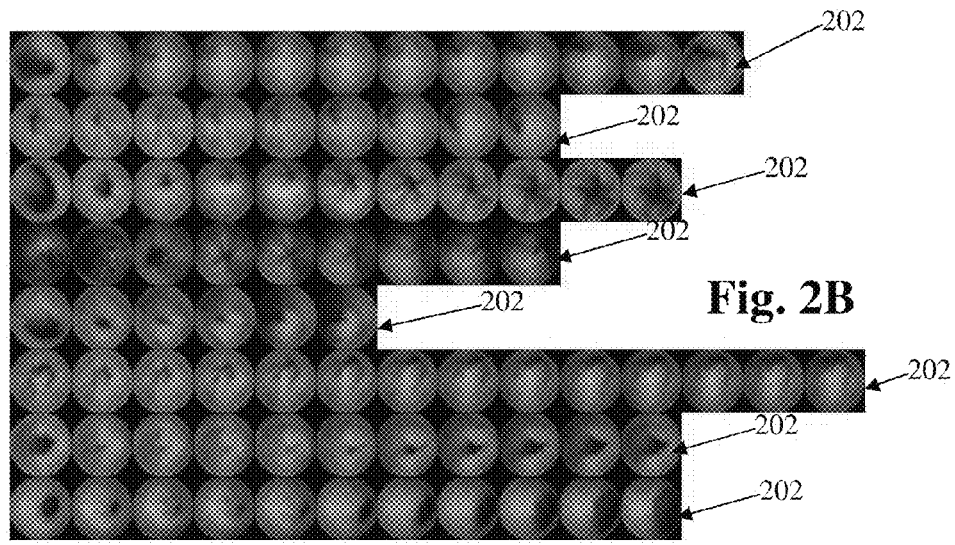

A moving image stream captured by the imaging device 40 may include scenes (e.g., a series of images depicting an event) or image sequences depicting predetermined or predicted events such as contractile activity of the body lumen walls (e.g., as shown in FIG. 2B).

Data processor 14 may include a detection module 22 for automatically detecting predetermined scenes or sequences using storage unit 19, an image database 10 and a logic detection database 20. Storage unit 19 may store images captured by imaging device 40. Image database 10 may store template or model sequence(s) each associated with a unique set of motility features or other known in-vivo events or scenes (e.g., such as the turbid sequences, bubble sequences, "wall" sequences, tunnel or static sequences, wrinkle sequences or and/contraction events shown in FIG. 2A). Logical detection database 20 may store instructions for execution or rules for use by software for comparing captured image(s) from storage unit 19 with the template sequence(s) from image database 10. Detection module 22 may use pattern recognition and/or feature extraction logic (for example, from logical detection database 20) to compare captured image frame sequences with template sequences.

Detection module 22 may be a physical device or may be instructions stored in a memory which when executed by a processor, e.g., data processor 14, may perform detection functions. For example, detection module 22 may be executed by a separate processor or may be a dedicated processing module.

Reference is made to FIGS. 2A and 2B, which show pictures of template sequences 200 and captured sequences 202, according to embodiments of the present invention.

A template or model sequence 200 (e.g., a scene or series of images depicting an event) may be a sequence of frames with pre-defined or pre-analyzed motility or diagnosis data that serve as a reference bank, to which captured endoluminal scene sequences may be compared for analysis. A query or captured sequence 202 may be an intestinal sequence, typically without pre-defined motility or diagnosis data, which may be compared to a template sequence 200 and may be assigned the motility or diagnosis data of one or more corresponding template sequences 200 if a match is found.

Template sequences 200 of FIG. 2A show different types of contractile scenes or events including, for example, a phasic occlusive contraction, a phasic semi-occlusive contraction, a sustained contraction, and a tunnel sequence (or no contraction). Template sequences 200 may include GI contraction patterns, such as small intestine (SI) contractions patterns, which may be among the motility patterns which may bear clinical pathological significance for GI disorders, such as ileus, bacterial overgrowth, functional dyspepsia and irritable bowel syndrome. GI contraction template sequences 200 may be classified in a number of ways to aid in diagnosis, for example, on the basis of their duration, repetition, frequency, score or similarity to a pre-defined sequence, etc.

Manually entering visual annotation of contractions from an image stream captured by an imaging device may be laborious due to the typically large number of image frames (e.g., 50,000 frames) collected as it passes through the GI tract. Furthermore, visual analysis by a physician may depend on the particular viewing physician and may be non-standardized, for example, providing differences based on human variation, when compared to other patient records or a previous image stream taken of the same patient.

Accordingly, embodiments of the invention may generate an automated and standardized system to analyze and annotate images.

Data processor 14 may automatically compare a set of captured sequences 202 of FIG. 2B with one of the template sequences 200 of FIG. 2A using standardized criteria. The processor may automatically match the most similar one or more of the plurality of captured sequences 202 to one or more template sequences 200. The processor may automatically assign the captured sequences 202 the contractile and/or motility data or metadata (e.g., phasic occlusive contraction) pre-associated with the matching template sequence 200.

The motility data assigned to captured sequences 202 may be used, for example, to automatically characterize motility and diagnose GI disorders in the patient from which the images were captured. Diagnosis of pathology and/or disorders may be based on, for example, number, size, frequency, distribution, symmetry, duration and/or geometrical pattern of contractions or other features along the intestinal tract. Other aspects of contractile activity may be inspected.

Contractile activity or sequences in an image stream may be tagged, flagged, marked, or otherwise indicated (and may be added to frames or sequences of frames as, e.g., metadata). For example, markers along a time bar or tissue color bar may visually indicate where along an image stream, image frames including contractile activity have been identified. In another example, hidden or non-visual markers, such as flags in a data register or cache, or with metadata associated with frames, may indicate contractile frames or segments. In some embodiments, a processor may automatically skip to the indicated frames for processing and/or a monitor may automatically skip to display the indicated frames. In other embodiments, statistical information summarizing the number, size, frequency, distribution, symmetry, duration and/or geometrical pattern of contractions may be provided and displayed to the user, for example, in addition to a range of normal or expected values of these parameters. Other methods of identifying image frames depicting contractile activity may be used.

Data processor 14 of FIG. 1 may use detection module 22 and logic from logic editing database 20 to align and compare captured sequences 202 with template sequences 200 of FIGS. 2A and 2B to identify patterns or trends having a pre-defined correlation with intestinal motility characteristics. For example, if a captured sequence 202 matches a template sequence 200 of, for example, a slow sequence of contractions (the intestinal passageway opens and closes with a slow periodicity), then the motility of the captured sequence 202 is likely slow.

However, as discussed, additional factors may affect the correct alignment and matching of captured sequence 202 and template sequence 200. Factors may include, for example, the direction or degree of contraction deformation, the speed of the imaging device, and imaging artifacts, such as, contractions events not captured that occur in between consecutive images, that are blocked by bubbles, or that are not in the imager field of view.

To account for these factors and accurately match the captured sequence 202 with a template sequence 200, embodiments of the invention may synchronize the sequences for comparison based on these factors. A processor may extract features from images and link images with similar features, for example, using pointers or indices. By aligning images in a sequence based on extracted anatomical features, instead of captured rate, embodiments of the invention may bypass imaging artifacts due to irregularities in the motion of the imaging device.

In one embodiment, a processor may assign one or more values or scores to rank the extracted features in each of one or more frames of the template and captured sequences 200 and 202. The processor may determine the differences between content scores assigned to each frame in the captured sequence 202 and each of a plurality of frames in the template sequence 200. The processor may determine the alignment between frames in the captured and template sequences 202 and 200 that minimizes the overall or cumulative difference in content scores throughout the sequences 200 and 202. This transformation may optimally synchronize the sequences 200 and 202 by aligning the most similar frames using scores associated with the anatomical content in the frames, the change in content between frames, and other factors affecting image motion. Thus, the true anatomical spacing of in vivo objects, not artifacts such as irregular imager motion, may determine the frame alignment.

In some embodiments, data processor 14 may align or link multiple frames of the captured sequence 202 to a single frame of the template sequence 200, or visa versa. These transformations may provide a many-to-one or one-to-many correspondence, respectively, between frames of the captured and template sequences 202 and 200. The correspondence type may fluctuate within the length of an individual captured sequence 202 or between consecutive captured sequences 202 through the length of the entire image stream.

Although sequences may be compressed or elongated for synchronization, frames should typically not be rearranged out of order since frames are generally not captured out of order. Accordingly, data processor 14 may align frames in a sequence to preserve the order of the frames. For example, if a frame (n) from the captured sequence 202 is aligned with a frame (m) from the template sequence 200, a subsequent frame (n+1) from the captured sequence 202 may only be aligned with the same and/or subsequent frame(s) (m), (m+1), (m+2), . . . , but not with a preceding frame (m−1) from the template sequence 200.

Once captured sequences 202 are found that best matches each template sequence 200 in the image stream, the processor may compile and analyze the associated motility data. The processor may input the motility data into a detection module (e.g., detection module 22 of FIG. 1), which may automatically determine a diagnosis based on statistical analysis of the motility data. The processor may assign the computer-determined diagnosis to the captured in vivo images.

The captured image stream, the motility data and/or the automatic diagnosis data may be displayed to a user, for example, on a digital display screen (e.g., monitor 18 of FIG. 1).

Figure 3:
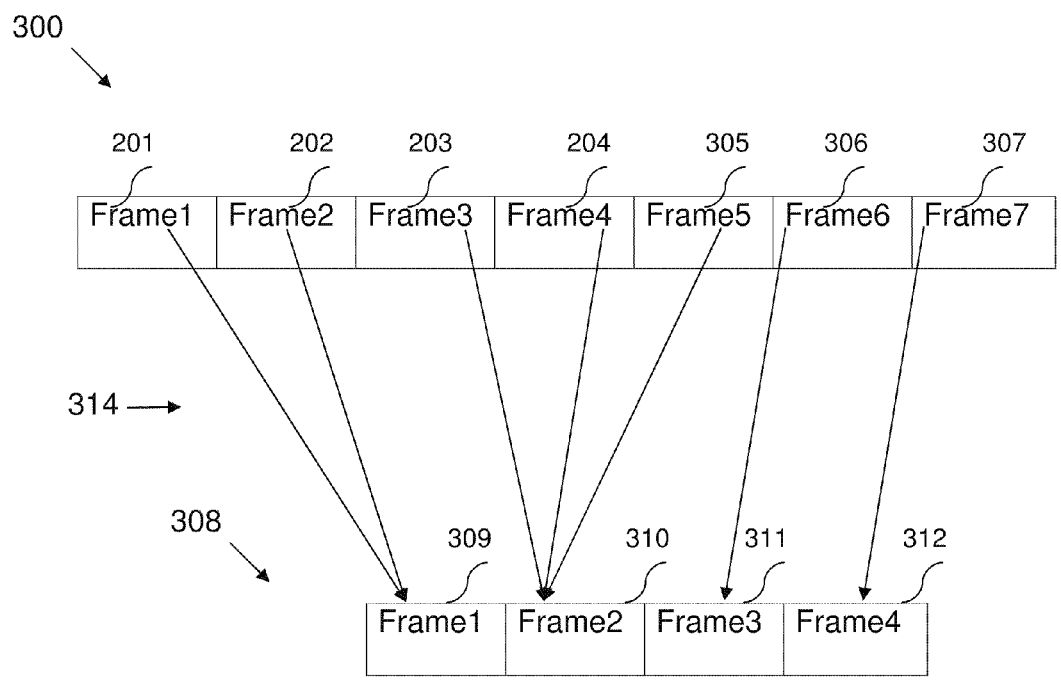
FIG. 3 is a schematic illustration of an alignment between a captured sequence and a template sequence, according to an embodiment of the invention.

Reference is made to FIG. 3, which schematically illustrates an alignment between a captured sequence 300 and a template sequence 308, according to an embodiment of the invention.

A processor may divide an initial image stream into a plurality of captured sequences 300. In some embodiments, sequences 300 may be sequence candidates identified and selected from the initial image stream. Each captured sequence may include a plurality of frames 301-307. The image stream may be divided regularly, generating captured sequences 300 of uniform length, or irregularly, generating captured sequences 300 of varying or non-uniform length.

In one embodiment, a processor may apply different sets or combinations of rules, criteria, and/or logic (e.g., selected from logic database 20 of FIG. 1) to divide the image stream into sequences 300 in different ways or to generate sequence candidates from the initial image stream. In one example, the processor may divide sequences based on scenes such as a contractile episode in which, for example, a plurality of contraction frames are within a maximum predetermined spacing from each other. In another example, the processor may divide sequences 300 based on color or illumination patterns. In another example, the processor may divide sequences 300 numerically, for example, so that each sequence 300 has an equal number of frames (although FIG. 3 shows captured sequences 300 with seven frames, other numbers of frames may be used).

The processor may synchronize captured sequences 300 and template sequences 308 using a map or transformation 314 aligning frames 301-307 and frames 309-312 to minimize the cumulative "energy" or difference in extracted feature scores between the frames. To determine the optimal or minimum energy map 314, the processor may compare each frame in the captured sequence with each frame or a plurality of frames in the template sequence 308 based on a plurality of predetermined criteria (e.g., as described in reference to FIG. 4).

Figure 4:
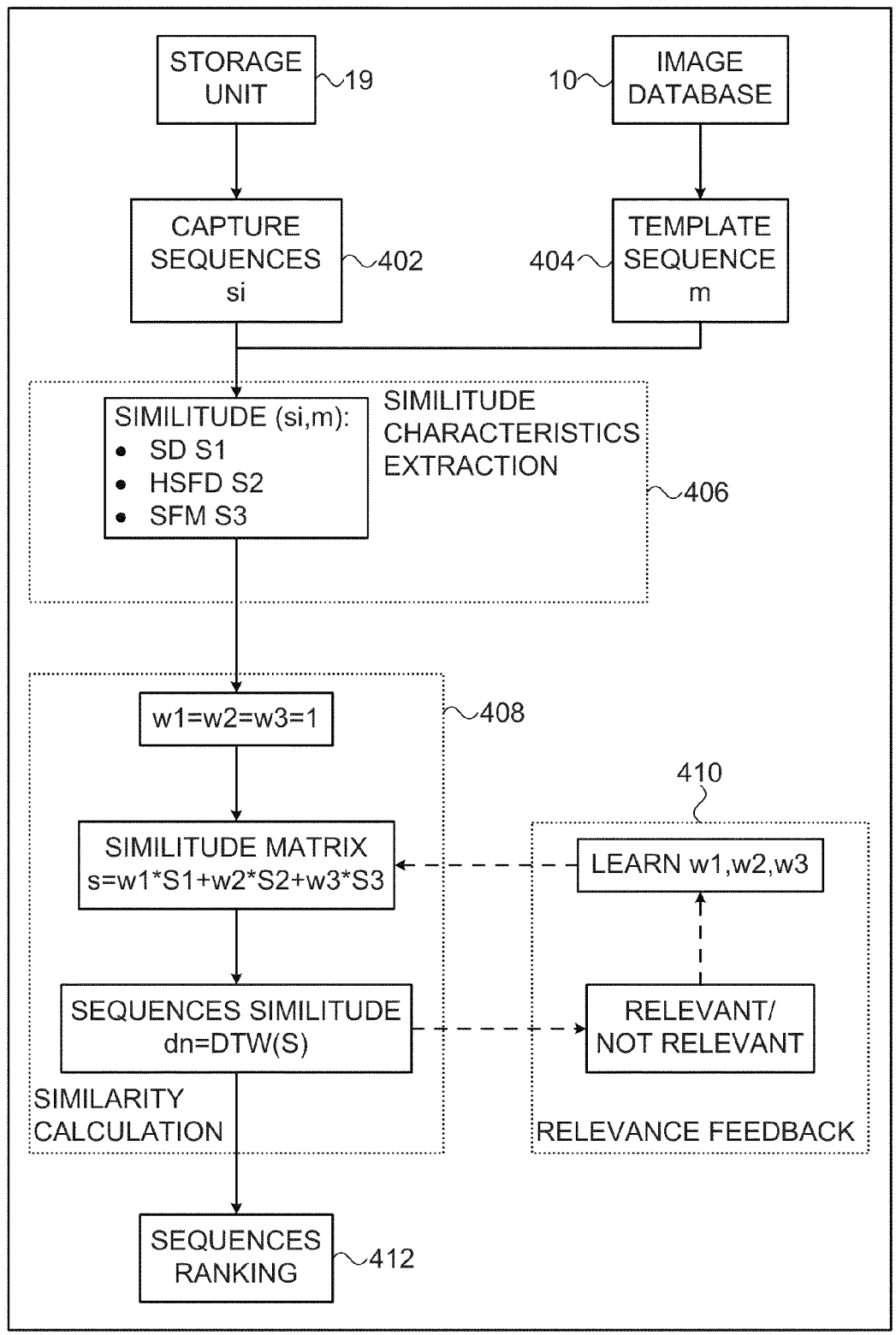
FIG. 4 is a flowchart of a method for synchronizing and comparing a captured sequence with a template sequence, according to an embodiment of the present invention.

Reference is made to FIG. 4, which is a flowchart of a method for synchronizing and comparing a captured or "query" sequence with a template or "model" sequence, according to an embodiment of the present invention.

Given a template sequence 404 (e.g., retrieved from image database 10 of FIG. 1) and a set of captured sequences 402 (e.g., divided from an image stream retrieved from storage unit 19 of FIG. 1), a processor may measure the similarity of each captured sequence 402 with respect to the template sequence 404. Based on the similarity measure, the processor may score, rate or rank the similarities of the captured sequence 402 with respect to the template sequence 404. This process may be repeated for all captured sequences 402 in the image stream or at least until a match or a predetermined number of matching captured sequences 402 are found. The processor may define a pairwise alignment between model and query sequences. Although some embodiments of the invention describe comparing a set of captured sequences to each template sequence, instead, a set of template sequences may similarly be compared to each captured sequence.

The processor may synchronize and compare the template and captured sequences using for example the following operations (other or different operations may be used):

In operation 406, the processor may extract similarity features;

In operation 408, the processor may estimate sequence similarity; and

In operation 410, the processor may execute relevance feedback for optimal weights assignment.

To extract similarity features in operation 406, the processor may evaluate and quantify the visual content of each frame by assigning (e.g., storing in association with frames) descriptors, scores, or other indicators of frame content. To account for skewed anatomical spacing in captured sequences, the processor may also assign "flow" descriptors that define and correct factors contributing to the skewed spacing, such as, intestinal deformation descriptors and irregular imager speed or motion descriptors. In one embodiment, similarity features of frames in a captured sequence may be evaluated and assigned, for example, SIFT (Scale-Invariant Feature Transform) descriptors. SIFT descriptors may encode visual image information, for example, at or associated with each pixel, and may be invariant to image scale and rotation. SIFT descriptors may provide robust matching across a substantial range of affine distortion, change in 3D view point, addition of noise, and change in illumination. Additionally or alternatively, another scoring or value system may be used to define the visual image information in the image frames.

In operation 406, the processor may determine the following descriptors for each frame or between frames (other descriptors and/or combinations of descriptor scores may be used):

$S_1$—SIFT Descriptors Difference (SDD) may measure similarity between image objects in the images.

$S_2$—Histogram of SIFT Flow Directions (HSFD) may describe transformation directions between consecutive images.

$S_3$—SIFT Flow Magnitude (SFM) may quantify an amount of intestine deformation between consecutive images.

The use of flow descriptors to characterize the motion of captured sequences enables the processor to align out-of-phase frames to accurately measure corresponding visual content in intestinal sequences. The flow descriptors may be directional. For example, horizontal flow descriptors may calculate content changes between (e.g., two) consecutive frames in the same captured sequence and vertical flow descriptors may calculate changes between frames in the template and captured sequences.

Figure 5:
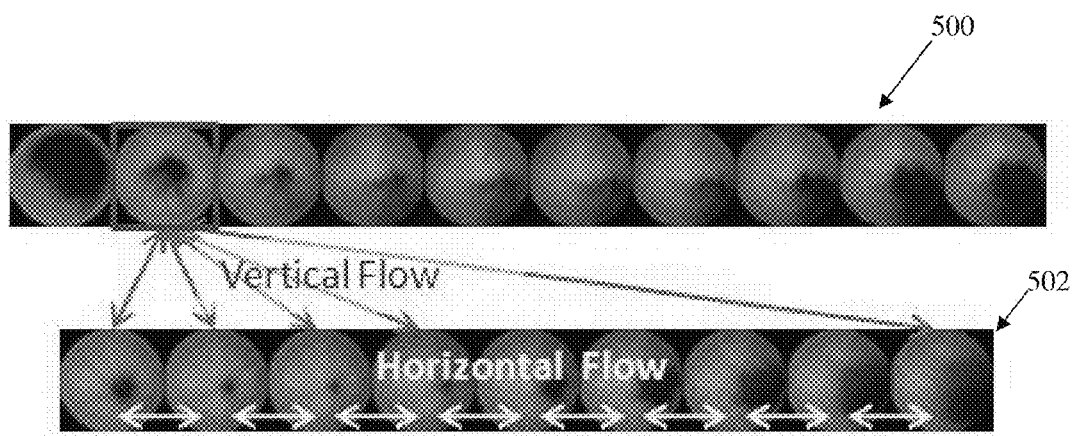
FIG. 5 is a schematic illustration of the directionality of horizontal flow in a sequence and vertical flow between two sequences, according to an embodiment of the invention.

Reference is made to FIG. 5, which schematically illustrates the directionality of horizontal flow descriptors in a sequence 502 and vertical flow descriptors between sequences 500 and 502, according to an embodiment of the invention. Calculating the vertical flow between sequences 500 and 502 may indicate an amount, score, "cost" or degree of deformation or transformation between corresponding structures in the images, which may be lower for images with more similar structures. On the other hand, calculating the horizontal flow within a sequence 502 may provide information about intestine deformation. Since similar sequences typically have similar deformation, similar horizontal flows may be used to align frames and identify matching sequences.

The SIFT Descriptors Difference, $S_1$, may be calculated using a vertical flow direction between sequences 500 and 502, while the Histogram of SIFT Flow Direction descriptor, $S_2$, and SIFT Flow Magnitude descriptor, $S_3$, may be calculated using a horizontal flow direction in each sequence 502. Alternatively, any of the descriptors may be calculated using horizontal, vertical or a combination of horizontal and vertical flow.

Figure 6:
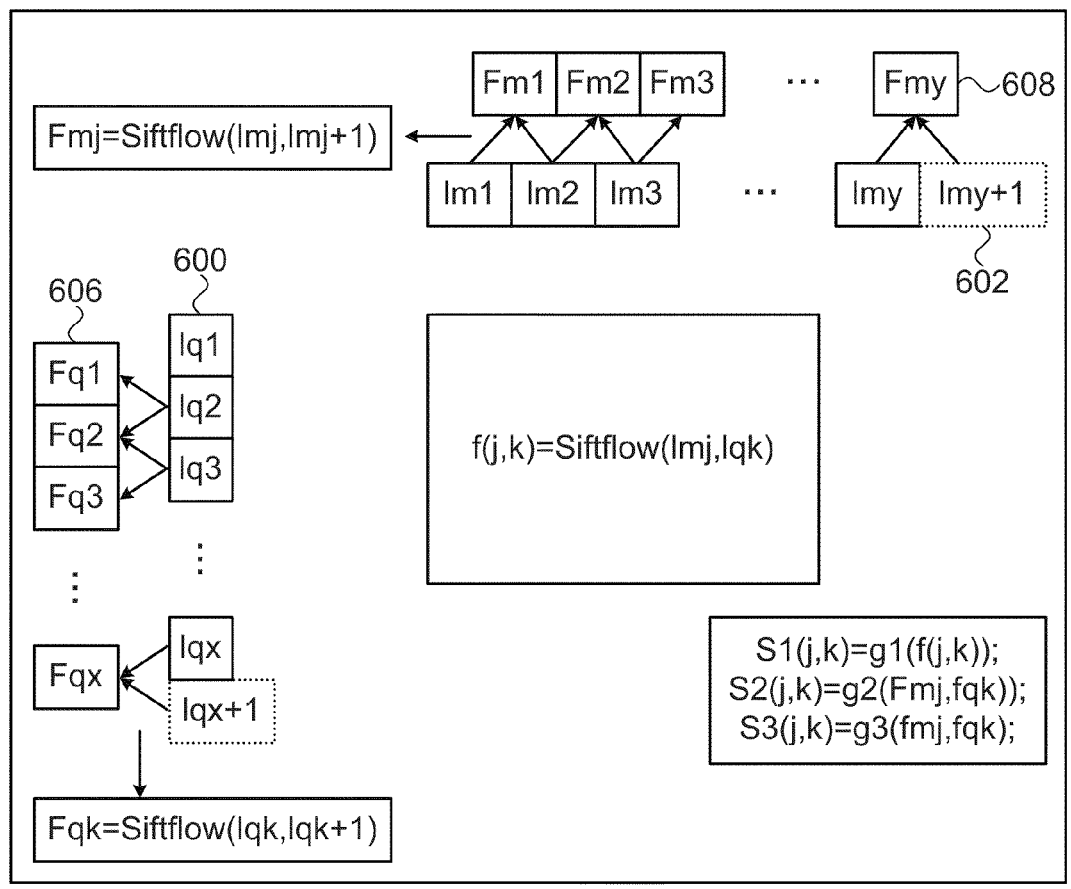
FIG. 6 is a schematic illustration of a data structure for calculating horizontal flow and vertical flow descriptors, according to an embodiment of the invention.

Reference is made to FIG. 6, which schematically illustrates a data structure for calculating horizontal flow and vertical flow descriptors, according to an embodiment of the invention.

A processor may retrieve a query or captured sequence 600 having a number (x) of query images (Iq) listed in sequence Iq1, . . . , Iqx, and a model or template sequence 602 having a number (y) of model images (Im) listed in sequence Im1, . . . , Imy. In one embodiment, an additional image (Iqx+1) may be added to the end of captured sequence 600 to calculate a horizontal flow difference value between the last (xth) frame in the sequence and a subsequent frame. Similarly, an additional image (Imy+1) may be added to the end of template sequence 602 to calculate a horizontal flow difference value between the last (yth) frame in the sequence and a subsequent frame. In this example, the number of horizontal difference values is the same as the number of frames (x) or (y) in sequence 600 and 602, respectively.

To compute the vertical flow, for example, for the SIFT Descriptors Difference, $S_1$, the processor may compute the difference between a (jth) frame in the template sequence 602 and a (kth) frame in the captured sequence 600. For the vertical difference between all combinations of frames (j) in sequence 602 and frames (k) in sequence 600, the processor may generate a matrix, where the (j,k)th entry is defined, for example, as follows:

$$S_1(j,k)=\|SD(Im_j)-SDAW(Iq_k)\|,$$

where SD may be a SIFT Descriptor of the template sequence and SDAW may be a SIFT Descriptor of the captured sequence 600 after its frames are warped or aligned with template sequence 602 and $\|\ \|$ may be the Euclidean norm. SIFT Descriptor $S_1(j, k)$ may be a vector of feature values or scores for a set of corresponding pixels in frames (j) in sequence 602 and frames (k) in sequence 600. Each element in $S_1(j, k)$ may describe a measure, rating or score of a feature or similarity between frame (j) in template sequence 602 and frame (k) in captured sequence 600. The processor may align the frames in the captured sequence 600 and template sequence 602 to minimize the difference in the descriptor values to align the most similar frames.

Figure 7:
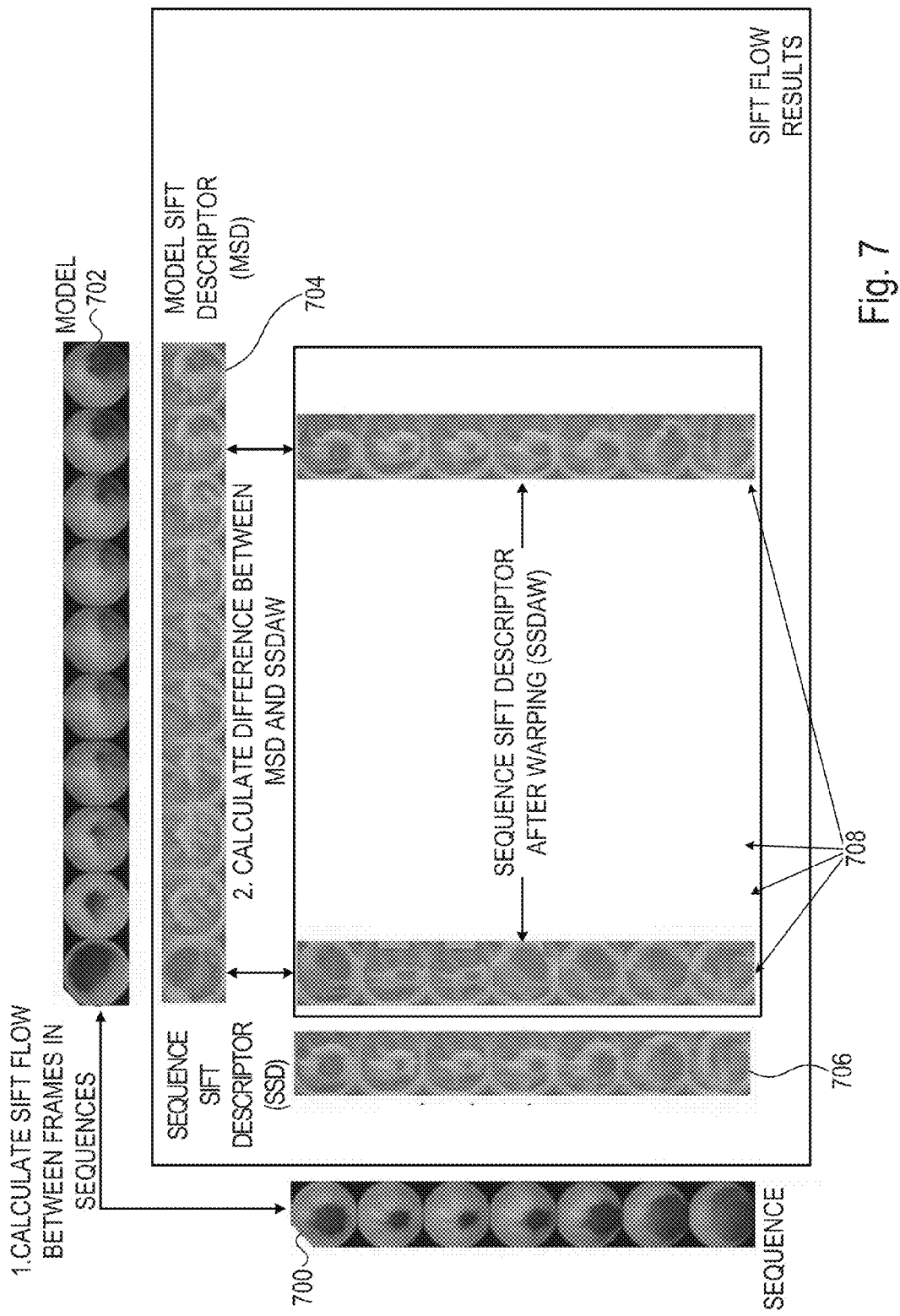
FIG. 7 is a schematic illustration of a data structure for computing vertical flow descriptors between a captured sequence and a template sequence, according to an embodiment of the invention.

Reference is made to FIG. 7, which schematically shows a data structure for computing a vertical flow descriptor, for example, the SIFT Descriptor Difference, $S_1$, between a captured sequence 700 and a template sequence 702, according to an embodiment of the invention.

To compute the descriptors of all combinations of frames, the processor may first extract the descriptor values (e.g., SIFT Descriptors) of template sequence 702 and captured sequence 700 to generate corresponding descriptor sequences 704 and 706, respectively.

The processor may compute descriptor sequences 708 (e.g., SIFT Descriptor After Warping (SDAW) sequences) of each of a plurality of different possible alignments of captured sequence 700 with respect to template sequences 702. The center descriptor sequence 708 may correspond to a one-to-one correspondence between the template and captured sequences 702 and 700, the descriptor sequences 708 to one side of center (e.g., for compressing alignments) may correspond to different many-to-one correspondences between the template and captured sequences 702 and 700, and the descriptor sequences 708 to the other side of center (e.g., for elongating alignments) may correspond to different one-to-many correspondences between the template and captured sequences 702 and 700. The alignments may preserve the order of frames in the sequences.

To align the template and captured sequences 702 and 700, the processor may compute the differences between the descriptor sequence 704 for frames in the template sequence and each of the descriptor sequences 708 for the different possible sequence alignments. The processor may select the alignment that corresponds to the minimum cumulative difference between the descriptor values of sequences 704 and 708. This alignment may synchronize corresponding content to generate in-phase sequences (e.g., if the one-to-one correspondence alignment is selected, the sequences were already in-phase).

The processor may define a match between the captured sequence 700 and the template sequence 702 with an alignment that generates the lowest cumulative descriptor difference value ($S_1$) or a cumulative difference value below (or above) a predetermined threshold. Other systems and processes may be used to compute the vertical flow between the template and captured sequences 702 and 700.

To compute the horizontal flow, for example, for the Histogram of SIFT Flow Direction descriptor, $S_2$, and SIFT Flow Magnitude descriptor, $S_3$, the processor may compute the difference between consecutive images in the same sequence. For the captured sequence 600, the processor may compute a sequence 606 of horizontal flow descriptors, Fqi, i=1, ..., x, defining the difference between consecutive images (Iqi) and (Iqi+1) in the captured sequence 600. Similarly for the template sequence 602, the processor may compute a sequence 608 of horizontal flow descriptors, Fmi, i=1, ..., y, defining the difference between consecutive images (Imi) and (Imi+1) in the template sequence 602. For the horizontal difference between each combination of adjacent pairs of frames (j) and (j+1) in the template sequence 602 and frames (k) and (k+1) in the captured sequence 600, the processor may generate a matrix to compare descriptors for all combinations of frames (j) and (k).

The Histograms of SIFT Flow Directions (HSFD), $S_2$, may provide information about the motion, angle, and/or directions of movement between frames to define the deformation or transformation between frames (j) and (k). Histogram of SIFT Flow Direction descriptors, $S_2$, may be calculated using horizontal flow. The processor may compute a matrix for the Histogram of SIFT Flow Direction descriptors, $S_2$, where the (j,k)th entry is defined, for example, as follows:

$$S_2(j,k)=\text{EMD}(\text{HSFD}(Fm_j)-\text{HSFD}(Fq_k)),$$

where (Fmj) is horizontal SIFT flow between frames (j) and (j+1) in the template sequence 602 and (Fqk) is horizontal SIFT flow between frames (k) and (k+1) in the captured sequence 600. In order to obtain similarity measures, the processor may compute an Earth Mover Distance (EMD) between histograms. Each element $S_2(j, k)$ quantifies the change in flow directions between frames (j) and (j+1) in the template sequence 602 and frames (k) and (k+1) in the captured sequence 600.

Figure 8:
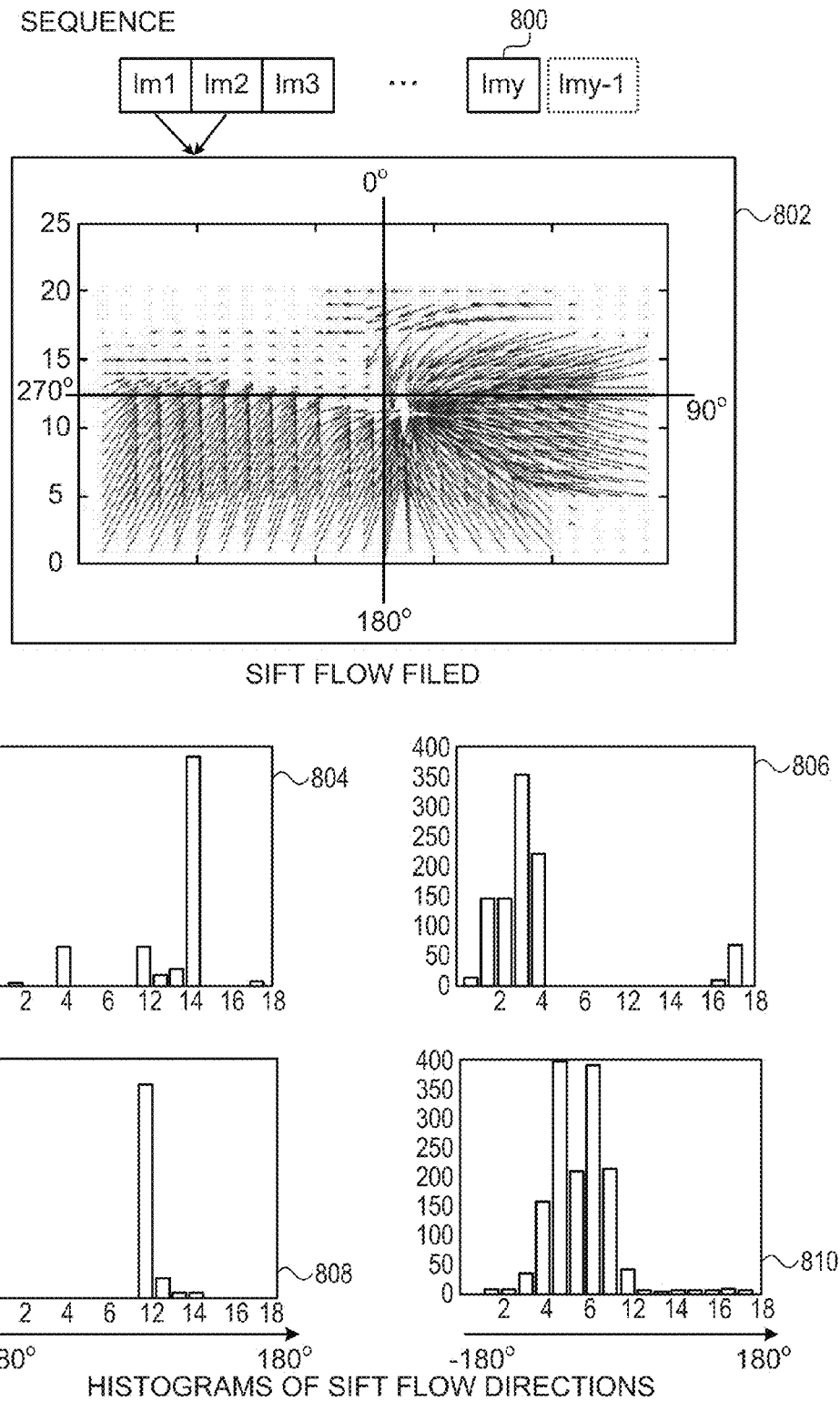
FIGS. 8 and 9 are schematic illustrations of data structures, each for computing horizontal flow descriptors, according to embodiments of the invention.

Reference is made to FIG. 8, which schematically illustrates a data structure for computing a horizontal flow descriptor, for example, the Histogram of SIFT Flow Direction descriptors, $S_2$, according to an embodiment of the invention.

For every pair of consecutive frames (i) and (i+1) in a sequence 800, the processor may generate a graph 802 of the directions of movement between the frames. From graph 802, the processor may generate one or more (e.g., four) histograms 804, 806, 808, and 810, where each histogram 804-810 may quantify the movement in a different one of a plurality of frame sub-regions (e.g., in each frame quadrant). Frames having similar change in the directions of movement between frames may have similar histogram profiles. Accordingly, the processor may match sequences based on the similarity in their respective histogram 804-810 profiles or corresponding scores. Although the sequence 800 shown in FIG. 8, (Im), refers to a model or template sequence, the same process may be used for query or captured sequence, (Iq).

Another horizontal flow descriptor, for example, the SIFT Flow Magnitude descriptor, $S_3$, may be used to quantify intestine deformation magnitude between consecutive frames. The SIFT Flow Magnitude descriptor, $S_3$, may quantify an amount a frame (i) has to be deformed to resemble the next consecutive frame (i+1) in the same sequence. This descriptor may quantify the intestine deformation for adjacent pairs of frames in the horizontal descriptor sequence 606 (Fmi) and sequence 608 (Fqk), for example, for the captured and template sequences 600 and 602, respectively.

The processor may generate a matrix to quantify the SIFT Flow Magnitude descriptor, $S_3$, for all combinations (j) and (k), where the (j,k)th entry may be defined, for example, as follows:

$$S_3(j,k)=\|\text{SFM}(Fm_j)-\text{SFM}(Fq_k)\|.$$

Each element $S_3(j, k)$ quantifies the change in the intestinal deformation magnitude between frames (j) and (j+1) in the template sequence 602 and frames (k) and (k+1) in the captured sequence 600. The horizontal flow quantifying the intestinal deformation between pairs of frames is smallest when the sequences 600 and 602 match.

Figure 9:
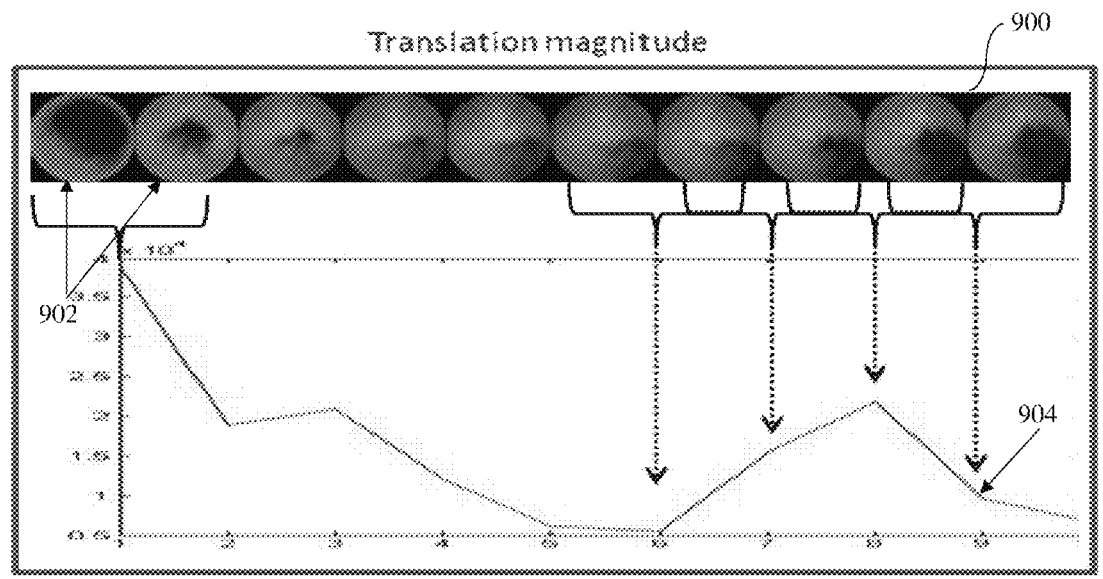

Reference is made to FIG. 9, which schematically shows a data structure for computing a horizontal flow descriptor, for example, the SIFT Flow Magnitude descriptor, $S_3$, according to an embodiment of the invention.

For every pair of consecutive frames (i) and (i+1) 902 in an image sequence 900, a processor may generate a descriptor value of the intestinal deformation magnitude between the frames. A profile 904 of the intestinal deformation descriptor values may be generated for each image sequence 900. When the sequence 900 is a template sequence, the profile 904 values may be SFM(Fmj), and when the sequence 900 is a captured sequence, the profile 904 values may be SFM(Fqk). The processor may use these values to generate the matrix to quantify the SIFT Flow Magnitude descriptor, $S_3$, for all frame alignment combinations (j) and (k) in sequences 600 and 602. The sequences 600 and 602 may be aligned to minimize the difference in their respective intestinal deformation profiles 904.

Referring again to FIG. 4, in operation 408, the processor may estimate sequence similarity. The processor may align the frames in the captured sequence 402 and template sequence 404 by minimizing the difference in descriptor values computed in operation 406. The processor may identify a match between one or more captured sequences 402 and the template sequence 404, for example, when the cumulative descriptor value therebetween (e.g., the difference in descriptor values between all aligned frames) is the absolute lowest, one of a predetermined number of the lowest cumulative difference values (e.g., from among a plurality of different captured sequences 402) or below a predetermined threshold.

In some embodiments, the cumulative descriptor value may measure a combination of descriptor values $S_1$, $S_2$, and/or $S_3$. To combine a plurality of descriptor values $S_1$, $S_2$, and/or $S_3$, the processor may combine the corresponding matrices [$S_1(j, k)$], [$S_2(j, k)$], and [$S_3(j, k)$] according to their respective weights to generate a matrix, S(j, k), where the (j,k)th entry may be defined, for example, as shown in operation 408 and as follows:

$$S(j,k)=w_1*S_1(j,k)+w_2*S_2(j,k)+w_3*S_3(j,k),$$

where ($w_1$), ($w_2$), and ($w_3$), are weights assigned to descriptors $S_1$, $S_2$, and/or $S_3$, respectively, j=1, ..., x, k=1, ..., y, and (x) and (y) are the lengths of the template sequence 404 and the captured sequence 402, respectively.

In operation 410 of FIG. 4, the processor may execute relevance feedback for optimal weights assignment. "Relevance feedback" may refer to an optimization of the descriptor weights for more accurate sequence matching. In relevance feedback, for a plurality of captured sequences 402 compared to a template sequence 404, the processor may retrieve an initial group of the N most similar captured sequences 402, for example, ordered by their degree of relevance and/or similarity to the template sequence 404. The processor may receive user input (e.g., via an input device) indicating whether or not frames currently displayed are, and to what degree, they are relevant to (matching) or irrelevant to (not matching) the template sequence 404. Based on the user input, the processor may re-calculate the weights of the different descriptors $S_1$, $S_2$, and/or $S_3$, so that the N images retrieved based thereon conform the user input, for example, including more of the frames marked relevant and fewer of the frames marked not relevant.

In one embodiment, the descriptor weights may be normalized with initial values, for example, $w_1=w_2=w_3=1$ (all weights are equal). The processor may compute a measure of the similarity, D, between a template sequence 404, (Ym), and a captured sequence 402, (Yq), for example, as follows:

$$D(Y_m, Y_q) = DTW(S(j,k)).$$

where each result D may be normalized by a pre-defined path-length using, for example, a dynamic time warping (DTW) calculation, to compare the template sequence 404 with captured sequences 402 having different lengths or numbers of frames. In one example, a smaller D value may indicate a better match between the template sequence 404 and captured sequences 402 (although a lager value of D may be equivalently used).

Once an initial set of captured sequences 402 matching the template sequence 404 is generated and displayed of a user interface via a monitor, a user may flag captured sequences as "relevant" or "not relevant" (e.g., corresponding to a flag or register value of 0 or 1, respectively), for example, using an input device such as input device 24 of FIG. 1. Based on this information, the processor may modify weights $w_1$, $w_2$ and $w_3$, for example, to minimize the distances D(Ym,Yq+) for relevant sequences and maximize the distances D(Ym,Yq−) to not relevant sequences. The optimization of weights, $w_i$, may use gradient descent calculations to minimize the energy function with respect to the weights, for example, as follows:

$$\sum_i \left( \sum_{q_j^+ \in Q^+} w_i * D_i(Y_m, Y_{q_j^+}) - \sum_{q_k^- \in Q^-} w_i * D_i(Y_m, Y_{q_k^-}) \right),$$

where $Yq_j^+$ are sequences marked as "relevant," $Yq_k^-$ are sequences marked as "non relevant". With the optimized weight values, the processor may re-calculate the matrix S(j, k) and may generate a new set of captured sequences 402 matching the template sequence 404. In some embodiments, the user may provide input defining relevant or irrelevant sequences only once, for example, to initialize the system, and the processor may modify and store the associated weights for subsequent use.

Embodiments of the invention may provide a system and method to compare each captured sequence in an image stream to models of pre-generated template sequences. For comparison, the captured sequences may be optimally aligned with each model. To align the captured and model sequences, frames may be linked based on several factors including, for example, the anatomical objects in the images, the direction of change between consecutive images, and the amount of intestinal distortion between consecutive images, which may in turn depend on the speed, rotation or way in which the imaging device moves through the digestion tract and any movement of the lumen walls themselves, such as contraction, stretching, compression, twisting and wrinkling.

Once the captured sequences are matched and aligned with the model sequences, the captured sequences and/or the corresponding matching model sequences may be displayed for the user and played, in sequence, as a moving image. The corresponding motility data may also be played in an integrated or adjacent display.

Figure 10:
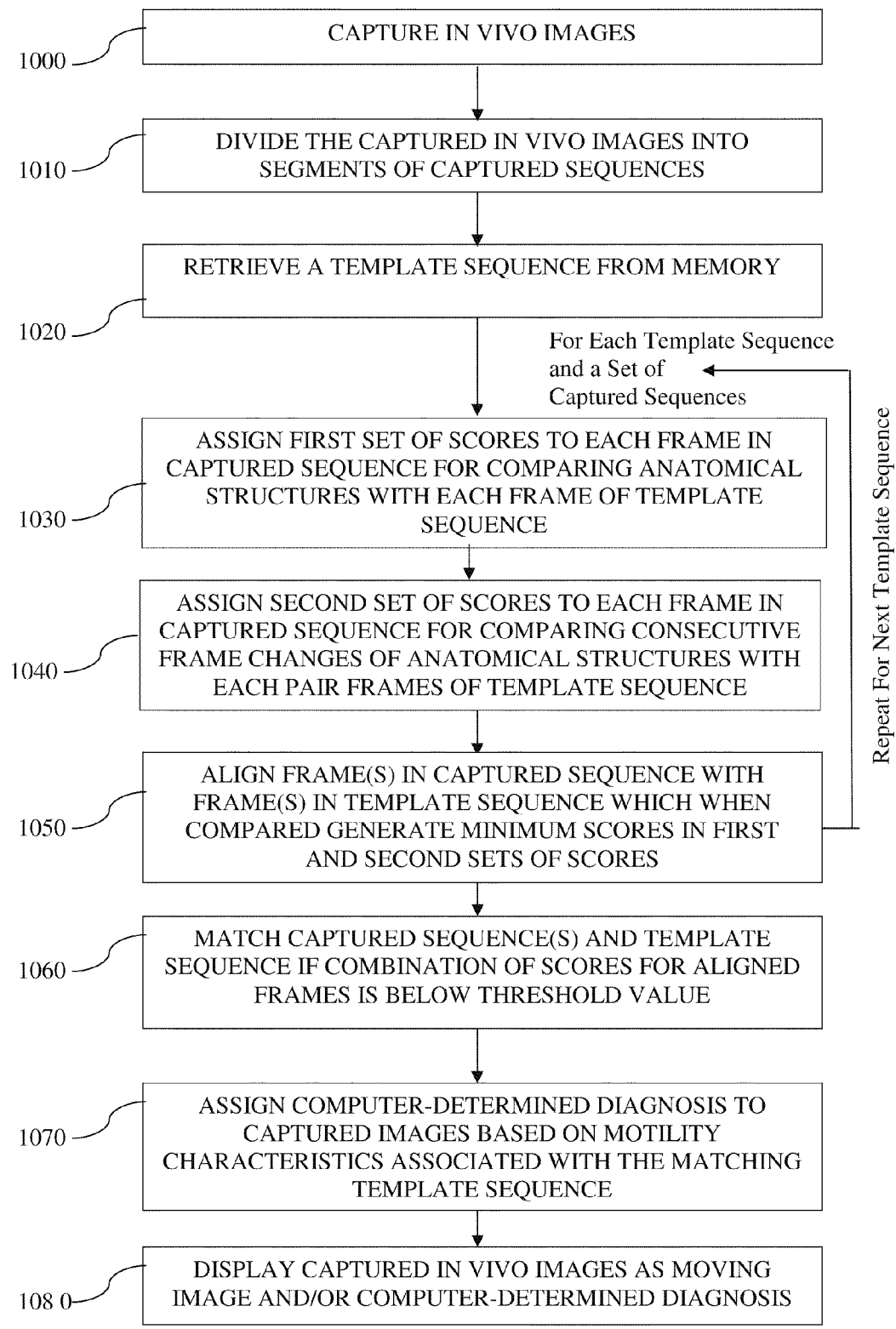
FIG. 10 is a flowchart of a method, according to an embodiment of the invention.

Reference is made to FIG. 10, which is a flowchart of a method for comparing sequences of in vivo images, according to an embodiment of the invention. Note that while the operations are described as being performed in sequence, they may be performed partially in parallel, or in a pipeline fashion.

In operation 1000, an autonomous imaging device (e.g., imaging device 40 of FIG. 1) may capture in vivo images while passively traversing the GI tract. The imaging device may include a transmitter, which may wireles sly transmits captured images while traversing the GI tract from inside a patient's body to a receiver disposed outside the patient's body. The captured images may be stored in a storage unit (e.g., storage unit 19 of FIG. 1) from which the processor may access the captured images.

In operation 1010, the processor may retrieve a plurality of captured images e.g., from a storage unit and divide them into a plurality of segments of sequential images.

In operation 1020, a processor (e.g., data processor 14 of FIG. 1) may retrieve a template sequence, for example, from a plurality of template sequences stored in a memory unit (e.g., image database 10 of FIG. 1). Each of the plurality of template sequences may be associated with different characteristics, for example pathological or motility characteristics, and may model different motility patterns to which a processor may compare and match sequences of the capture in vivo images. In one example, the template sequences may model different types of contractions of the endoluminal tissue wall.

The template sequence may be automatically retrieved by the processor using criteria selected by a human operator or by an automatic retrieval process identifying the most relevant template sequences. For example, a processor may automatically determine and/or receive input from a user (e.g., via input device 24 of FIG. 1) indicating a target or possible diagnosis for a motility disorder (e.g., or more specifically for the presence of a certain disease, such as IBS-C). In this example, the processor may retrieve a template sequence associated with motility characteristics related to the target diagnosis or disease.

For each captured image sequence, in operation 1030, the processor may assign a first set of scores, values or ratings to each frame in the captured sequence. Each score in the first set of scores may be generated based on a comparison of anatomical structures of the frame in the captured sequence and anatomical structures of a different or unique frame in the retrieved template sequence. The score or rating system may define the content of different combinations of frames in the captured sequence and the template sequence. In one example, the first set of scores may include vertical flow descriptor scores, such as, the SIFT Descriptors Difference score, $S_1$, described in reference to FIGS. 6 and 7.

For each captured image sequence, in operation 1040, the processor may assign a second set of scores, values or ratings to each frame in the captured sequence. Each score in the second set of scores may be generated based on a comparison of a change in anatomical structures between the frame in the captured sequence and a frame in the captured sequence consecutive thereto and a change in anatomical structures between a pair of consecutive frames in the retrieved template sequence. In one example, the second set of scores may include horizontal flow descriptor scores, such as, the Histogram of SIFT Flow Direction descriptor score, $S_2$, and/or the SIFT Flow Magnitude descriptor score, $S_3$, described in reference to FIGS. 6 and 8, 9, respectively.

In some embodiments, the processor may determine the difference values based on a similarity in anatomical imaged structures in the frames, a direction of change of the image objects between consecutive frames in each sequence, and an amount of intestinal deformation between consecutive frames in each sequence.

In operation 1050, for these sequences, the processor may align each frame in the captured sequence with one or more frames in the template sequence for which the comparisons therebetween generate the minimum scores in the first and second sets of scores. Each frame in the captured sequence may be aligned with one or more frames in the template sequence using a one-to-many or a many-to-one correspondence. The processor may align the frames using a linking index, pointer, metadata, or memory bank storing the correspondence between frames. The processor may transform the frames of the captured and template sequences so that the frames which had out-of phase content, have in-phase content. The processor may align frames in a way that preserves the order of frames in the sequences.

Operations 1030-1050 may be repeated for each captured sequence or segment extracted from an image stream captured in vivo.

In operation 1060, the processor may define a match between the template sequence and one or more of the plurality of captured sequences if the combination of scores in the first and second sets of scores for the frames in the captured sets compared with the one or more aligned frames in the template sequence is below a threshold value. The threshold value may be the combined score for all captured sequences, or the lowest predetermined number of combined score for matching a predetermined number of captured sequences to each template sequence, or a predetermined threshold.

The processor may weigh the scores for each frame from the first and second sets of scores differently to generate a new set of captured sequences matching the template sequence, for example, to more closely match user-selected captured sequences.

In operation 1070, the processor may assign a computer-determined diagnosis to the image stream or to specific segments thereof, including the captured in vivo images or a portion thereof (e.g., the captured sequence) based on the motility characteristics associated with the template sequences that match the captured image sequences. A diagnosis or score may be assigned to the entire image stream (e.g., a score indicating abnormal motility of the GI tract), to images imaging a certain region of the GI tract (e.g., a score indicating abnormal contractions of the small bowel), or to individual images, segments or sequences of images imaging the GI tract.

In operation 1080, a monitor (e.g., monitor 18 of FIG. 1) may display the captured in vivo images, in sequence, as a moving image, the descriptor values associated with the frames, the motility characteristics associated with the matching template sequences, and/or the computer-determined diagnosis. The monitor may display the captured in vivo images at a viewing rate proportional to the rate at which they were captured. Alternatively, the monitor may display the captured in vivo images at a standardized rate or the rate of the matching template sequence. In some embodiments, a user may enter a control command, which when received by the processor switches between the captured and standardized viewing rates. The monitor may display the motility characteristics and/or computer-determined diagnosis assigned in operation 1070. In some embodiments, the motility characteristics and/or the associated descriptor values may be displayed as a map, table, or profile adjacent to the corresponding sequences through the image stream.

Other operations, orders of operations, and methods of comparing a captured image stream to template in-vivo sequences may be used. Various specific sets of methods may be combined in different embodiments and the method of FIG. 10 may be executed alone or in combination with other processes described herein.

When used herein, a "score" or "rank" may be a general rating, where (in one embodiment) the closer the scores between frames or sequences the greater the overall similarity therebetween, and (in another embodiment) a score may be associated with a specific property, e.g., a color score, a pathology score, a contraction type, a direction of image change, an amount of intestinal deformation between consecutive frames, or another score or measure that indicates a specific feature in the sequences. The individual scores of the frames may be combined as an average score measuring the similarity between the sequences. A similarity scores may represent, for example, a (normal or weighted) average of the difference in features between the captured and template sequences.

When used herein, a scene, sequence, or anatomical event may for example, include a plurality of frames depicting an in-vivo event such as a contraction (e.g., symmetric with equal duration of lumen opening and closing or asymmetric when opening and closing occurs at different speeds), a static sequence, a wrinkle sequence, or any other sequence. Each sequence may have the same or different length(s).

When used herein, displaying images "in sequence" may refer to displaying images in sequential or consecutive time slots and in substantially the same spatial position on a screen or display, for example, so that the images appear as a moving image stream.

Although embodiments of the invention describe assigning descriptor scores to each frame or frame pair, scores may similarly be assigned to each region of a frame, frame quadrant, individual pixel or pixel set, for example, of a 4×4 or 16×16 pixel block.

The frames may be analyzed for scoring, synchronizing, and matching, in a non-compressed form (analyzing absolute pixel values) and/or a compressed form (analyzing changes and relative pixel values). A compressed data header or other summary frame information package may indicate associated descriptor value(s). Compression mechanisms known in the art for expressing spatial changes within a frame or temporal changes between consecutive frames may be used.

It may be appreciated that although the frame analysis may be made after processing, frames may also be analyzed in "real-time" during frame capture and transmission.

It is noted that while embodiments of the invention described herein are adapted for imaging of the GI tract, the devices and methods disclosed herein may be adapted for imaging other body cavities or spaces.

Different embodiments are disclosed herein. Features of certain embodiments may be combined with features of other embodiments; thus certain embodiments may be combinations of features of multiple embodiments.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A system for comparing sequences of in vivo images, the system comprising:
   a memory to store a plurality of template sequences each associated with a different set of pre-defined intestinal motility characteristics;
   a processor to:
      retrieve a template sequence from the memory,
      receive in vivo images captured by an autonomous in vivo imaging device, and
      divide the captured in vivo images into a plurality of captured image sequences, wherein for each of the plurality of captured sequences, the processor is to:
         assign a first set of scores to each frame in the captured sequence, wherein each score in the first set of scores is based on a comparison of anatomical structures of the frame in the captured sequence and anatomical structures of a frame in the retrieved template sequence;
         assign a second set of scores to each frame in the captured sequence, wherein each score in the second set of scores is based on a comparison of a change in anatomical structures between the frame in the captured sequence and a frame in the captured sequence consecutive thereto and a change in anatomical structures between a pair of consecutive frames in the retrieved template sequence; and
         align each frame in the captured sequence with one or more frames in the template sequence for which the comparisons therebetween generate the minimum scores in the first and second sets of scores, and wherein for the plurality of captured image sequences, the processor is to:
      define a match between the template sequence and one or more of the plurality of captured sequences if the combination of scores in the first and second sets of scores for the frames in the captured sets compared with the one or more aligned frames in the template sequence is below or above a threshold value; and
      a display to display the captured in vivo images, in sequence, as a moving image stream.

2. The system of claim 1, wherein the processor assigns a computer-determined diagnosis to the captured in vivo images based on the motility characteristics associated with the matching template sequence.

3. The system of claim 1, wherein the processor aligns the frames of the captured and template sequences so that frames having similar content are in-phase.

4. The system of claim 1, wherein the processor determines the scores based on the similarity in anatomical imaged structures in the frames, a direction of change of the image objects between consecutive frames in each sequence, and/or an amount of intestinal deformation between consecutive frames in each sequence.

5. The system of claim 1, wherein the processor aligns the frames using a one-to-many or a many-to-one correspondence between at least some frames in the captured and template sequences.

6. The system of claim 1, wherein the processor aligns the frames to preserve the order of frames in the sequences.

7. The system of claim 1, wherein the processor weighs the different scores to generate a new set of captured sequences matching the template sequence to more closely match user-selected captured sequences.

8. The system of claim 1, wherein the memory stores template sequences that model contractions of the endoluminal wall.

9. The system of claim 1, wherein the system comprises a receiver and the imaging device comprises a transmitter, wherein the transmitter wirelessly transmits the captured images while traversing the GI tract from inside a patient's body to the receiver disposed outside the patient's body.

10. The system of claim 1, wherein the display displays the captured in vivo images at a viewing rate proportional to the rate at which they were captured.

11. The system of claim 1, wherein the display displays the captured in vivo images at a standardized rate of the matching template sequence.

12. A method for synchronizing sequences of in vivo images, the method comprising:
   retrieving one of a plurality of template sequences from a memory, where each template sequence is associated with a different pre-defined set of intestinal motility characteristics;
   for each of a plurality of captured image sequences from an image stream captured by an autonomous in vivo device:
      assigning a first set of scores to each frame in the captured sequence, wherein each score in the first set of scores is based on a comparison of anatomical structures of the frame in the captured sequence and anatomical structures of a frame in the retrieved template sequence;
      assigning a second set of scores to each frame in the captured sequence, wherein each score in the second set of scores is based on a comparison of a change in anatomical structures between the frame in the captured sequence and a frame in the captured sequence consecutive thereto and a change in anatomical structures between a pair of consecutive frames in the retrieved template sequence; and
      aligning each frame in the captured sequence with one or more frames in the template sequence for which the comparisons therebetween generate the minimum scores in the first and second sets of scores;
   for the plurality of captured image sequences, defining a match between the template sequence and one or more of the plurality of captured sequences if the combination of scores in the first and second sets of scores for the frames in the captured sets compared with the one or more aligned frames in the template sequence is below or above a threshold value; and
   displaying the captured in vivo images, in sequence, as a moving image stream.

13. The method of claim 12, comprising assigning a computer-determined diagnosis to the captured in vivo images based on the motility characteristics associated with the matching template sequence.

14. The method of claim 12, wherein the frames of the captured and template sequences are aligned so that frames having similar content are in-phase.

15. The method of claim 12, wherein the scores are determined based on the similarity in anatomical imaged structures in the frames, a direction of change of the image objects between consecutive frames in each sequence, and/or an amount of intestinal deformation between consecutive frames in each sequence.

16. The method of claim 12, wherein the frames of the captured and template sequences are aligned using a one-to-many or a many-to-one correspondence between at least some frames in the captured and template sequences.

17. The method of claim 12, wherein the frames of the captured and template sequences are aligned to preserve the order of frames in the sequences.

18. The method of claim 12, wherein the different scores are weighed to generate a new set of captured sequences matching the template sequence to more closely match user-selected captured sequences.

19. The method of claim 12, wherein the template sequences model contractions of the endoluminal wall.

20. The method of claim 12, wherein the captured in vivo images are displayed at a viewing rate proportional to the rate at which they were captured.

21. The method of claim 12, wherein the captured in vivo images are displayed at a standardized rate of the matching template sequence.

* * * * *